(12) United States Patent
Wei et al.

(10) Patent No.: US 9,078,832 B2
(45) Date of Patent: Jul. 14, 2015

(54) BIOMIMETIC SCAFFOLD FOR BONE REGENERATION

(71) Applicants: Mei Wei, Mansfield, CT (US); Zengmin Xia, Coventry, CT (US)

(72) Inventors: Mei Wei, Mansfield, CT (US); Zengmin Xia, Coventry, CT (US)

(73) Assignee: THE UNIVERSITY OF CONNECTICUT, Farmington, CT (US)

(*) Notice: Subject to any disclaimer, the term of this patent is extended or adjusted under 35 U.S.C. 154(b) by 140 days.

(21) Appl. No.: 13/848,893

(22) Filed: Mar. 22, 2013

(65) Prior Publication Data

US 2013/0251762 A1    Sep. 26, 2013

Related U.S. Application Data

(60) Provisional application No. 61/685,689, filed on Mar. 22, 2012.

(51) Int. Cl.
| | |
|---|---|
| *A61L 27/46* | (2006.01) |
| *A61L 27/56* | (2006.01) |
| *C08L 89/00* | (2006.01) |
| *A61K 38/39* | (2006.01) |
| *A61K 9/70* | (2006.01) |

(52) U.S. Cl.
CPC . *A61K 9/70* (2013.01); *A61K 38/39* (2013.01); *A61L 27/46* (2013.01); *A61L 27/56* (2013.01); *A61L 2430/02* (2013.01)

(58) Field of Classification Search
CPC ..... A61L 27/46; A61L 2430/02; A61L 27/56; C08L 89/00; A61K 38/39; A61K 9/70
See application file for complete search history.

(56) References Cited

U.S. PATENT DOCUMENTS

| | | | |
|---|---|---|---|
| 4,888,366 | A | 12/1989 | Chu et al. |
| 5,205,921 | A | 4/1993 | Shirkanzadeh |
| 6,136,369 | A | 10/2000 | Leitao et al. |
| 6,139,585 | A | 10/2000 | Li |
| 6,187,047 | B1 | 2/2001 | Kwan et al. |
| 6,207,218 | B1 | 3/2001 | Layrolle et al. |
| 6,569,489 | B1 | 5/2003 | Li |
| 6,887,488 | B2 | 5/2005 | Cui et al. |
| 6,974,862 | B2 | 12/2005 | Ringeisen et al. |
| 7,087,086 | B2 | 8/2006 | Li et al. |
| 7,153,938 | B2 | 12/2006 | Kikuchi |
| 7,879,093 | B2 | 2/2011 | Wei et al. |
| 8,003,611 | B2 | 8/2011 | Kamitakahara et al. |
| 8,007,854 | B2 | 8/2011 | Wei et al. |
| 8,084,095 | B2 | 12/2011 | Wei et al. |

(Continued)

FOREIGN PATENT DOCUMENTS

| | | |
|---|---|---|
| CN | 1451444 A | 10/2003 |
| CN | 1528468 A | 9/2004 |

(Continued)

OTHER PUBLICATIONS

Neel et al. (Soft Matter 2006;2:986-992).*

(Continued)

*Primary Examiner* — Ernst V Arnold
(74) *Attorney, Agent, or Firm* — Cantor Colburn LLP

(57) ABSTRACT

Described herein are novel methods of producing collagen-apatite (Col-Ap) scaffolds that exhibit a unique, anisotropic multi-level lamellar structure in which nano and submicron pores in each lamellae and macro pores are co-aligned.

20 Claims, 3 Drawing Sheets

(56) References Cited

U.S. PATENT DOCUMENTS

| | | |
|---|---|---|
| 2002/0018797 A1 | 2/2002 | Cui et al. |
| 2002/0018798 A1 | 2/2002 | Sewing et al. |
| 2002/0143398 A1 | 10/2002 | Osaka et al. |
| 2004/0258729 A1 | 12/2004 | Czernuszka et al. |
| 2006/0204491 A1 | 9/2006 | Kokubo et al. |
| 2006/0216494 A1 | 9/2006 | Furedi-Milhofer et al. |
| 2007/0255422 A1 | 11/2007 | Wei et al. |
| 2009/0061887 A1 | 3/2009 | Hart et al. |
| 2009/0130168 A1 | 5/2009 | Wei et al. |
| 2009/0130456 A1 | 5/2009 | Wei et al. |
| 2009/0149634 A1 | 6/2009 | Shoji et al. |
| 2011/0287167 A1 | 11/2011 | Wei et al. |
| 2012/0003280 A1 | 1/2012 | Wei et al. |

FOREIGN PATENT DOCUMENTS

| | | |
|---|---|---|
| EP | 1566186 A1 | 8/2005 |
| WO | 2004024201 A2 | 3/2004 |
| WO | 2004040036 A1 | 5/2004 |
| WO | 2004040037 A1 | 5/2004 |
| WO | 2007055431 A1 | 5/2007 |
| WO | 2009061887 A2 | 5/2009 |
| WO | 2009061908 A2 | 5/2009 |

OTHER PUBLICATIONS

Deville (Materials 2010;3:1913-1927).*
Landi et al. "Porous Hydroxyapatite/Gelatine Scaffolds with Ice-Designed Channel-Like Porosity for Biomedical Applications"; Acta Biomaterialia; 4; pp. 1620-1626; (2008).
International Search Report and Written Opinion: International Application No. PCT/US2013/033443; International Filing Date Mar. 22, 2013; Date of Mailing Jul. 9, 2013; 13 pages.
Barrere et al.; "Influence of Ionic Strength and Carbonate on the Ca-P Coating Formation from SBF×5 Solution"; Biomaterials; 23; pp. 1921-1930; (2002).
Barrere et al.; "Nucleation of Biomimetic Ca-P Coatings on Ti6A14V From a SBF × 5 Solution: Influence of Magnesium"; Biomaterials; 23; pp. 2211-2220; (2002).
BR2002000698; Aug. 24, 2004; application No. BR2002-698, filed Feb. 6, 2002; English Abstract only.
Bradt et al.; "Biomimetic Mineralization of Collagen by Combined Fibril Assembly and Calcium Phosphate Formation"; Chem. Mater.; 11; pp. 2694-2701; (1999).
Chen et al.; "PLLA Scaffolds With Biomimetic Apatite Coating and Biomimetic Apatite/Collagen Composite Coating to Enhance Osteoblast-like Cells Attachment and Activity"; Surface & Coatings Technology; 201; pp. 575-580; (2006).
Chen et al., Biomimetic Coating of Apatite/Collagen Composite on Poly L-lactic Acid Facilities Cell Seeding; Conf. Proc. IEEE Eng. Med. Biol. Soc.;vol. 4, pp. 4087-4090, (2006) Abstract, 1 page.
Chen et al.; "Composite Coating of Bonelike Apatite Particles and Collagen Fibers on Poly L-Lactic Acid Formed Through an Accelerated Biomimetic Coprecipitation Process"; J. Biomed. Biomater. Res B, Appl. Biomater., 77, pp. 315-322; (2006).
Doi et al., "Osteonectin Inhibitin gDe Novo Formation of Apatite in the Presence of Collagen"; Calcif Tissue Int.; 44; pp. 200-208; (1989).
Fan et al.; "A Composite Coating by Electrolysis-Induced Collagen Self-Assembly and Calcium Phosphate Mineralization"; Biomaterials; 26; pp. 1623-1632; (2005).
Gross et al.; "The Heat Precipitation of Collagen from Neutral Salt Solutions: Some Rate-Regulating Factors"; The Journal of Biological Chemistry; 233(2); pp. 355-360; (1958).
Kim et al.; "Bonding Strength of Bonelike Apatite Layer to Ti Metal Substrate"; Journal of Biomedical Materials Research; 38(2); pp. 121-127; (1997) Abstract only.
Kokubo et al., "Ca, P-rich Layer Formed on High-strength Bioactive Glass-ceramic A-W", J. of Biomedical Materials Research; 24; pp. 331-343 (1990).
Kokubo et al.; "Solutions Able to Reproduce In Vivo Surface-structure Changes in Bioactive Glass-ceramic A-W3"; Journal of Biomedical Materials Research; 24; pp. 721-734; (1990).
Liu et al.; "Biomimetic Coprecipitation of Calcium Phosphate and Bovine Serum Albumin on Titanium Alloy"; Journal of Biomedical Materials Research Part A; 57(3); pp. 327-335; (2008).
Qu et al.; "Improvement of Bonding Strength Between Biomimetic Apatite Coating and Substrates"; Published online in Wiley InterScience, Journal of Biobased Materials and Bioenergy (www.interscience.wiley.com). DOI: 10.1002(jbm.b.30889); 9 pages; (2007).
Qu et al.; "The Effect of Initial pH on Morphology of Biomimetic Apatite Coating"; Key Engineering Materials vols. 330-332; pp. 757-760; (2007).
Qu et al.; "Synthesis of Dense Collagen/Apatite Composites Using a Biomimetic Method"; Journal of American Ceramic Society; 91(10); pp. 3211-3215; (2008).
Qu et al.; "The Effect of Temperature and Initial pH on Biomimetic Apatite Coating"; Journal of Biomedical Materials Research Part B: Applied Biomaterials; 87B, pp. 204-212; (2008).
Thompson; "Buffers"; Pharmaceutics (Part I); pp. 15-20; Spring (2004).
Yanli et al.; "Formation of Bonelike Apatite-Collagen Composite Coating on the Surface of NiTi Shape Memory Alloy"; Scripta Materialia; 54; pp. 89-92; (2006).
Yu et al.; "Incorporation of Bovine Serum Albumin Into Biomimetic Coatings on Titanium with High Loading Efficacy and its Release Behavior"; J Mater Sci: Mater Med; 20; pp. 287-294; (2009).
Zhang et al.; "Hierarchical Self-Assembly of Nano-Fibrils in Mineralized Collagen"; Chem. Mater.; 15; pp. 3221-3226; (2003).

* cited by examiner

BIOMIMETIC SCAFFOLD FOR BONE REGENERATION

CROSS-REFERENCE TO RELATED APPLICATIONS

This application claims priority to U.S. Provisional Application 61/685,689 filed on Mar. 22, 2012, which is incorporated herein by reference in its entirety.

STATEMENT REGARDING FEDERALLY SPONSORED RESEARCH & DEVELOPMENT

This invention was made with government support under Grant #CBET 1133883 awarded by the National Science Foundation (NSF) and under Grant #AR 059962 awarded by the National Institutes of Health (NIH). The government has certain rights in the invention.

FIELD OF THE DISCLOSURE

The present disclosure is in the field of compositions and methods for tissue engineering, and more specifically for bone regeneration.

BACKGROUND

Collagen-apatite (Col-Ap) composites resembling the composition of natural bone have been studied extensively and are considered as promising bone tissue engineering materials. Apatite exhibits good biocompatibility, osteoconductivity and bone-bonding ability, but its brittleness, rigidity, and low degradation rate limit its usefulness in broader applications. Collagen, the most abundant protein of extracellular matrix, is chemotactic to fibroblasts. It shows high affinity to cells and good resorbability in vivo. Nevertheless, its poor mechanical strength has restricted its usage in load-bearing applications. By adding apatite to collagen, the mechanical properties of the resulting composite could increase substantially. It was also reported that Col-Ap composite scaffolds demonstrate better osteoconductive properties and higher levels of osteogenic gene expression than non-mineralized collagen scaffolds.

Many approaches to the production of Col-Ap scaffolds have been developed, however, what is needed are Col-Ap scaffold of defined structure and methods of making the structures.

BRIEF SUMMARY

In one aspect, included herein is a method of producing a structural protein-calcium phosphate scaffold with an anisotropic lamellar pore structure, comprising providing a structural protein-calcium phosphate hydrogel; compressing the structural protein-calcium phosphate hydrogel to increase the structural protein density in the hydrogel; freezing the hydrogel with a temperature gradient in a transverse direction across the hydrogel; and drying the frozen hydrogel to produce the structural protein-calcium phosphate scaffold with an aligned lamellar structure. In specific aspects, the structural protein is collagen and the calcium phosphate is hydroxylapatite. Also included are the products of the processes described herein.

In another aspect, included herein is a biomimetic structural protein-calcium phosphate scaffold with an anisotropic lamellar pore structure, wherein at the macro-level, the scaffold comprises an anisotropic lamellar pore structure and a co-aligned macro-pore size of 10 to 350 micrometers, and at the micro-level each lamella of the lamellar structure comprises uniaxial aligned layers of structural protein fibers mineralized with the calcium phosphate having a micro-pore size of less than 1 micrometer.

In a further aspect, a method of bone repair comprises contacting the structural protein-calcium phosphate scaffold with an anisotropic lamellar pore structure with osteoprogenitor cells, bone marrow cells, or both, under conditions suitable to repair bone.

BRIEF DESCRIPTION OF THE DRAWINGS

Referring now to the drawings wherein like elements are numbered alike in several FIGURES.

Figure 1:
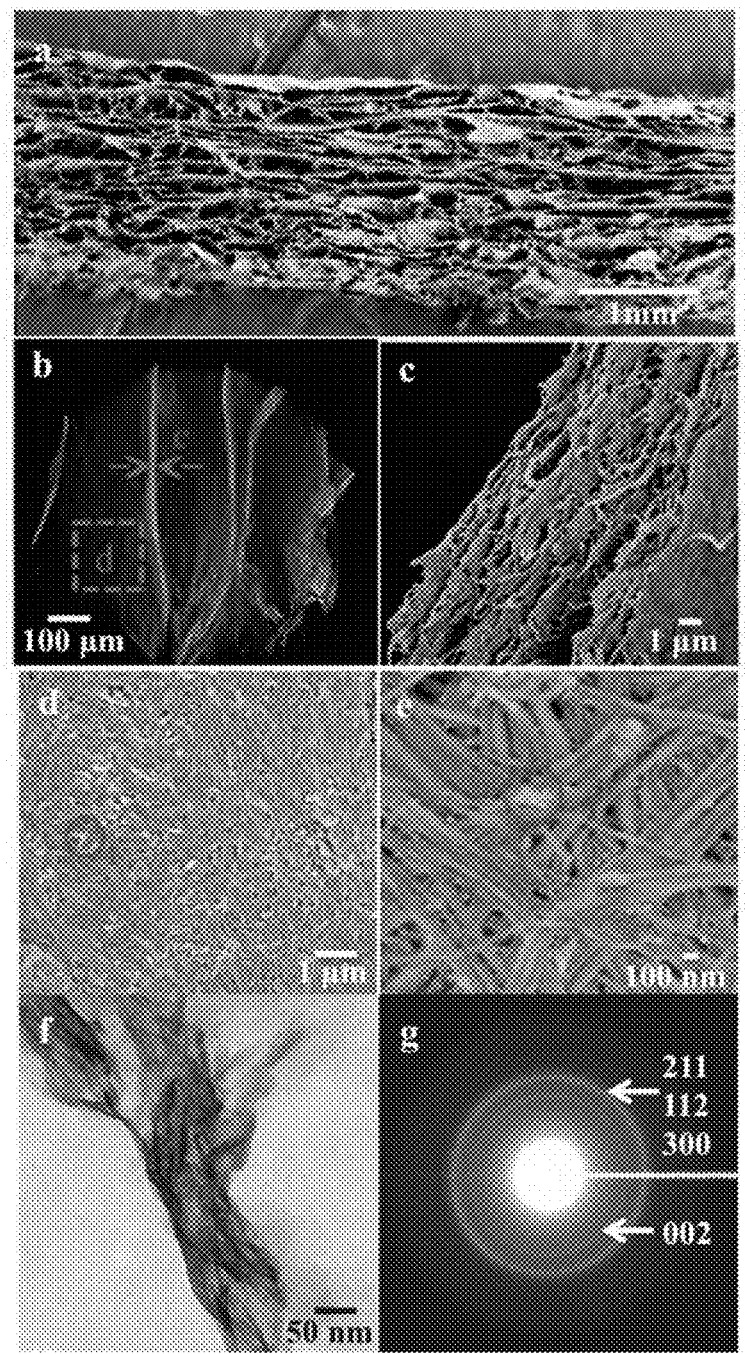
FIG. 1 (a, c-e) show FESEM images of a collagen-apatite scaffold. (b) MicroCT of 3-dimensional reconstruction of a collagen-apatite scaffold. The scaffold possesses a multi-level lamellar structure having (a and b) co-aligned macro-pores, (c) nano and submicro-pores, and (d and e) a biomimetic surface containing mineralized fibril bundles. (f) TEM image demonstrating needle-like apatite crystallites throughout the cross-section of collagen fibers similar to those found in natural bone, (g) High magnification of selected area electron diffraction patterns exhibits typical rings of low crystalline apatite structure. (The Miller indices for each corresponding ring are labeled)

The above-described and other features will be appreciated and understood by those skilled in the art from the following detailed description, drawings, and appended claims.

DETAILED DESCRIPTION

Described herein are novel methods of producing scaffolds such as collagen-apatite (Col-Ap) scaffolds that exhibit a unique multi-level lamellar structure in which nano and sub-micron pores in each lamella and macro-pores are co-aligned. This multi-level lamellar structure leads to a higher active surface area, improved permeability to oxygen and nutrients, and faster removal of metabolic waste compared to the conventional uniaxial pore structure. Another unique property of the scaffold is the combination of a long-range ordered surface morphology and 3-D porous structure. In one aspect, the surface of the scaffold comprises mineralized collagen fibrils with a length of over a few millimeters. In this aspect, the mineralized collagen fibrils are further organized into big bundles, the diameter of which can be tailored by gelation conditions in terms of temperature and initial collagen concentration.

The novel structural protein-calcium phosphate scaffold with an anisotropic lamellar pore structure has a unique macro and micro-level structure. At the macro-level, the scaffold exhibits an anisotropic lamellar pore structure and a co-aligned pore size of 10 to 350 micrometers. At the micro-level, each lamella of the lamellar structure includes uniaxial aligned layers of structural protein fibers mineralized with the calcium phosphate having a micro pore size of less than 1 micrometer. The porosity of the scaffolds can be greater than 85%. In one embodiment, the scaffold protein is collagen and the calcium phosphate is hydroxylapatite. In another embodiment, the wall thickness of the lamellar layers is 2 to 30 micrometers. An advantage of the methods described herein is that the wall thickness is tunable depending on the conditions used to produce the scaffold. In yet another embodiment, the scaffold exhibits fewer visual bridges between the lamellar layers than observed in previous structures. The basic building block of the multi-level lamellar structure described herein is a network of long and interconnected mineralized collagen fibers. The length of each fiber can be extended to a few centimeters, such as greater than 5 centimeters.

In one aspect, a method of producing a structural protein-calcium phosphate scaffold (e.g., collagen-hydroxylapatite, Col-Ap) with an anisotropic lamellar pore structure comprises providing a structural protein-calcium phosphate hydrogel; compressing the structural protein-calcium phosphate hydrogel to increase the structural protein density in the hydrogel; freezing the hydrogel with a temperature gradient in a transverse direction across the hydrogel; and drying the frozen hydrogel to produce the structural protein-calcium phosphate scaffold with an aligned lamellar structure.

Compression of the hydrogel raises the chemical potential of the hydrogel and causes water to be exuded from the hydrogel. Without being held to theory, it is believed that in the compression process, the fluid leaving surface acts as a filter along which compacted lamellae of mineralized collagen fibrils are aligned.

In one embodiment, compression is self-compression performed, for example, temperature of 4 to 45° C. and a time of 5 minutes to 5 hours. Self-compression is performed, for example, by removing the hydrogel from a container and allowing it to undergo unconfined self-compression. As used herein, unconfined self-compression means uniaxial loading without lateral confining pressures. Alternatively, compression can be performed by placing a weight on the hydrogel. A compressive load can be applied, for example, by placing a piece of thick glass/metal plate on top of the hydrogel for 5 minutes to 5 hours. The collagen concentration in the hydrogel can be tailored by the mass of the plate. In one aspect, compression leads to an increase of the collagen concentration in the hydrogel thereby increasing the Young's modulus of the freeze dried hydrogel by 5-30-fold.

After compression, the hydrogel is frozen with a temperature gradient in a transverse direction across the hydrogel. Freezing can be accomplished in a mold that allows for control of the temperature in the transverse direction. An exemplary mold is a copper mold with its cover and bottom made from Teflon®. As the temperature gradient advances, the advancing ice front causes diminishing liquid, pushing the structural protein-calcium phosphate to higher concentrations. The ice front applies shear stress on the network of the hydrogel which increase the degree of the alignment of mineralized structural protein fibril arrays in each lamella.

In practice, freezing with a temperature gradient in a transverse direction across the hydrogel can be accomplished using a cylindrical mold designed as follows. The top and bottom of the cylindrical mold are made from heat insulating materials (Teflon®) to reduce heat transfer from the surrounding environment to the gel. The wall of the mold is made from materials with high thermal conductivity (copper) to create the thermal gradient transversely form the edges to the center of the gel.

In one embodiment, the freezing temperature is −197° C. to −10° C. In another embodiment freezing takes place over 0.5 to 4 hours. In one aspect, the cooling rate during freezing is 1 to 40° C./min.

Once the compressed hydrogel is frozen, it is dried under vacuum conditions, such as in a freeze-drying apparatus, to produce the structural protein-calcium phosphate scaffold with an aligned lamellar structure. In one aspect, the drying temperature is −10 to −80° C. and the pressure in the vacuum chamber is 0.2 to 3 mbr, the drying time is 10 to 120 hours. In one embodiment, after drying, the structural protein-calcium phosphate scaffold with an anisotropic lamellar pore structure has a structural protein content of 40 to 99 wt % or higher.

In one aspect, a structural protein-calcium phosphate hydrogel is prepared in a one-step process. The method involves preparing an aqueous system containing water, $Ca^{2+}$, $HPO_4^{2-}$, structural protein (e.g., a collagen such as collagen type I), a weak acid (e.g., acetic acid, and the like) and a buffer system; and optionally one or more of the following ions: $Mg^{2+}$, $Na^+$, $K^+$, $Cl^-$, $SO_4^{2-}$, $HCO_3^-$; wherein the aqueous system has an initial pH of about 6 to about 8. The aqueous system is allowed to stand, for example at a temperature of about 4° C. to about 45° C., for a period of greater than one hour, specifically greater than 10 hours, to form a hydrogel. The gel is optionally crosslinked, isolated.

The structural protein includes known structural protein such as collagens, elastin, and keratins, specifically collagen, and more specifically acetic acid soluble collagen, including Types I, II, III, and V, and yet more specifically collagen Type I. In one embodiment, the concentration of structural protein in the aqueous system is 1 g/L to 10.0 g/L.

There is no particular limitation as to the source of the structural protein. The structural protein may be obtained from commercial sources or extracted from natural sources using procedures well known in the art.

The aqueous system used to prepare the structural protein-calcium phosphate hydrogel generally comprises the following inorganic ions: $Ca^{2+}$ and $HPO_4^{2-}$; and optionally one or more of the following ions: $Mg^{2+}$, $Na^+$, $K^+$, $Cl^-$, $SO_4^{2-}$, $HCO_3^-$. The aqueous system can be prepared by dissolving, in an aqueous solvent, salt that when disassociated will result in the particular ions $Ca^{2+}$, $Mg^{2+}$, $Na^+$, $K^+$, $Cl^-$, $SO_4^{2-}$, $HPO_4^{2-}$ and $HCO_3^-$. The aqueous solvent can be deionized and purified water. Exemplary salts include those that result in an aqueous solution of the desired ions, for example, alkali metal halides, alkaline earth metal halides, alkali metal hydrogen carbonates, alkali metal phosphates, and alkali metal sulfates. Specific salts include NaCl, KCl, $K_2HPO_4$, $MgCl_2$, $Na_2SO_4$, $CaCl_2$ and $NaHCO_3$.

The particular concentrations of each of the above-described ions initially present in the aqueous system can be as follows: $Ca^{2+}$ at about 0.1 to about 30.0 mM, specifically about 1 to about 15.0 mM, and more specifically about 5 to about 10.0 mM; $Mg^{2+}$ at about 0 to about 10.0 mM, specifically about 0.5 to about 5.0 mM, and more specifically about 1.0 to about 3 mM; $Na^+$ at about 0 to about 300.0 mM, specifically about 50.0 to about 200.0 mM, and more specifically about 80.0 to about 150.0 mM; $K^+$ at about 0 to about 20.0 mM, specifically about 1.0 to about 15.0 mM, and more specifically about 4.0 to about 10.0 mM; $Cl^-$ at about 0 to about 300.0 mM, specifically about 50.0 to about 200.0 mM, and more specifically about 80.0 to about 150.0 mM; $SO_4^{2-}$ at about 0 to about 5.0 mM, specifically about 0 to about 1.5 mM, and more specifically about 0 to about 0.6 mM; $HPO_4^{2-}$ at about 0.05 to about 20.0 mM, specifically about 0.1 to about 10.0 mM, and more specifically about 0.5 to about 5.0 mM; and $HCO_3^-$ at about 0 to about 50.0 mM, specifically about 5.0 to about 30.0 mM, and more specifically about 10.0 to about 20.0 mM.

An additional component present in the aqueous system used to prepare the structural protein-calcium phosphate hydrogel is a buffer system. The buffer system can contain HEPES (4-(2-hydroxyethyl)-1-piperazineethanesulfonic acid or N-2-hydroxyethylpiperazine-N'-2-ethanesulfonic acid; Molecular formula: $C_8H_{17}N_2SO_3$; CAS No: 7365-45-9) and an alkali metal hydrogen carbonate (e.g. $NaHCO_3$, $KHCO_3$, etc.) which are added to the aqueous system in amounts to substantially stabilize the aqueous system. The concentration of HEPES present in the aqueous system can be at about 5.0 grams per liter (g/L) to about 80.0 g/L, specifically about 10.0 g/L to about 60.0 g/L, and more specifically about 12.0 g/L to about 48.0 g/L.

Additional buffer systems include tris-hydroxymethyl aminomethane (TRIS), HEPES salts, piperazine-1,4-bis(2-ethanesulfonic acid) (PIPES), PIPES salts, combinations of the foregoing with an alkali metal carbonate, and combinations thereof.

The aqueous system may optionally contain additional ionic components such as silicate, strontium, zinc, silver, fluoride, combinations thereof, and the like.

The weak acid present in the aqueous system used to prepare structural protein-calcium phosphate hydrogel is an acid with a pKa of about 3.5 to about 5.5. Exemplary acids include organic acids, specifically alkyl carboxylic acids such as acetic acid, propionic acid, and the like.

The aqueous system can have an initial pH of about 6 to about 8, specifically about 7 to about 7.5.

Various crosslinking agents, such as a carbodiimide, can be used to crosslink the structural protein in the hydrogel. Exemplary crosslinking agents include glutaraldehyde, 1-ethyl-3-[3-dimethylaminopropyl]carbodiimide hydrochloride optionally in combination with N-hydroxysuccinimide or N-hydroxysulfosuccinimide; dimethyl suberimidate, bis(sulfosuccinimidyl)suberate ($BS^3$), 3,3'-dithiobis(sulfosuccinimidylpropionate) (DTSSP), sulfosuccinimidyl-4-(N-maleimidomethyl)cyclohexane-1-carboxylate (Sulfo-SMCC), dithiobis(succinimidyl)propionate (DSP), sulfosuccinimidyl 6-(3'-[2-pyridyldithio]-propionamido)hexanoate, and the like. In specific embodiment, the amount of crosslinking agent used is about 0.1 to about 0.4 M, specifically about 0.2 to about 0.3 M. The hydrogel can be crosslinked before or after drying.

In one embodiment, a method of forming a structural protein-calcium phosphate hydrogel comprises forming an aqueous system comprising a structural protein, a weak acid, water, $Ca^{2+}$, $Mg^{2+}$, $Na^+$, $K^+$, $Cl^-$, $SO_4^{2-}$, $HPO_4^{2-}$, $HCO_3^-$ and a buffer system, wherein the aqueous system has an initial pH of about 6 to about 8, in container; and allowing the structural protein-calcium phosphate hydrogel to form in the container.

The resulting hydrogel generally contains hydroxylapatite, but can also be other types of calcium phosphate. Exemplary calcium phosphate minerals include $Ca_5(PO_4)_{3-x}(OH)_{1-y}(CO_3)_{x+y}$, $Ca_5(PO_4)_3(OH)$, $Ca_3(PO_4)_2$, $CaHPO_4$, $Ca(H_2PO_4)_2$, and the like.

In one embodiment, the novel scaffolds described herein further comprise a drug such as a drug that can improve the bone-regeneration properties of the scaffold. Drugs can be incorporated into the scaffold by adding drug to m-SBF or depositing the drug at the surface of freeze-dried scaffolds. Exemplary drugs for incorporation into the scaffolds include antibiotics and antiseptics (e.g., gentamicin, tetracycline, minocycline), vitamins (e.g., riboflavine), and the like.

In one aspect, the novel scaffold described herein is used in methods of bone repair. In one aspect, a method of bone repair comprises contacting the novel scaffold described herein with osteoprogenitor cells, bone marrow cells, or both, under conditions suitable to repair bone. Contacting can be in vitro or in vivo in a host. Bone repair can include new bone formation, bone-redistribution, bone-host integration, scaffold degradation, or a combination thereof.

In one aspect, the novel collagen-apatite scaffolds can be tested in a double-hole mouse calvarial model for evaluating new bone formation. A series of transgenic mice harboring GFP reporters that mark different levels of osteoprogenitor lineage differentiation have been developed. The pOBCol3.6GFP transgene is activated at an early stage of preosteoblast differentiation and continues being expressed strongly in osteoblasts lining on new bone surfaces. The development of transgenic mice harboring type I collagen GFP reporters and the ability to reserve the fluorescent signal during histological processing make it possible to use transgenic mice to evaluate host/donor cell behavior during cell-based bone healing. In this study, multiple types of cells from different tissue sources, including both osteoprogenitor cells (OPCs) and bone marrow cells (BMCs), are used in combination with scaffolds for bone regeneration. New bone formation can be observed by microscopy techniques either with single cell type or multiple cell types. Without being held to theory, the amount of new bone formed, bone distribution, new bone-host bone integration, and scaffold degradation may be distinctly different among these groups. According to the results from fluorescence imaging analysis and H&E histology, new bone formation can be confirmed.

The invention is further illustrated by the following non-limiting examples.

Example 1

Preparation of and Characterization of Col-Ap Hydrogel

The biomimetic collagen-apatite hydrogel was synthesized using a collagen containing modified simulated body fluid (m-SBF; 109.5 mM $Na^+$, 6 mM $K^+$, 1.5 mM $Mg^{2+}$, 7.5 mM $Ca^{2+}$, 110.0 mM $Cl^-$, 17.5 mM $HCO_3^{2-}$, 3.0 mM $HPO_4^{2-}$, 50 mM HEPES). The concentration of collagen in m-SBF was adjusted to 2 g/L to achieve an apatite content of 35% in the scaffold (wt %). The collagen concentration in the m-SBF can be tailored to provide scaffolds with different apatite contents. The pH of the m-SBF solution was adjusted to 7 by addition of HEPES (4-(2-hydroxyapatiteethyl)-1-piperazineethanesulfonic acid) and NaOH. The collagen-apatite hydrogel was prepared using a two temperature process. In this process, the solution was incubated in a sealed vial at 25° C. for 1 h, the temperature was then increased at a rate of 0.5° C./min to 40° C. and left at 40° C. for 22.5 h.

The collagen-apatite hydrogel was allowed to undergo unconfined self-compression at room temperature for different time periods. Because the compression force applied by self-gravity raised the chemical potential of water inside the hydrogel, water was exuded from the gel. The mineralized collagen fibrillar density of the gel can be easily controlled by changing the self-compression time. External compression force can also be applied, for example, by placing a weight on top of the hydrogel.

The collagen-apatite gel was made in a custom-made mold which can control the temperature gradient in the transverse direction. The top and bottom of the mold were made from Teflon® to reduce heat transfer from the surrounding environment to the gel. The wall of the mold was made from copper to create a thermal gradient transversely form the edge to the center of the gel. The mold was placed in a chamber precooled to −10° C. to −180° C. The temperature in the cold chamber was varied intending to modify the spacing between each lamella.

The as-frozen hydrogel was then lyophilized in a freeze dryer. The freeze-dried scaffolds were subsequently cross-linked with 1 wt % N-(3-dimethylaminopropyl)-N'-ethylcarbodiimide (EDC) hydrochloride for 24 h. Then scaffolds were rinsed thoroughly in distilled water, followed by rinsing with 5% glycine solution, rinsing again with water, and finally freeze-drying for a second time.

FIG. 1 (a, c-e) show FESEM images of a collagen-apatite scaffold. (b) MicroCT of 3-dimensional reconstruction of a collagen-apatite scaffold. The scaffold possesses a multi-level lamellar structure having (a and b) co-aligned macropores, (c) nano and submicro-pores, and (d and e) a biomimetic surface containing mineralized fibril bundles. (f) TEM image demonstrating needle-like apatite crystallites throughout the cross-section of collagen fibers similar to those found in natural bone, (g) High magnification of selected area electron diffraction patterns exhibits typical rings of low crystalline apatite structure. (The Miller indices for each corresponding ring are labeled)

Figure 2:
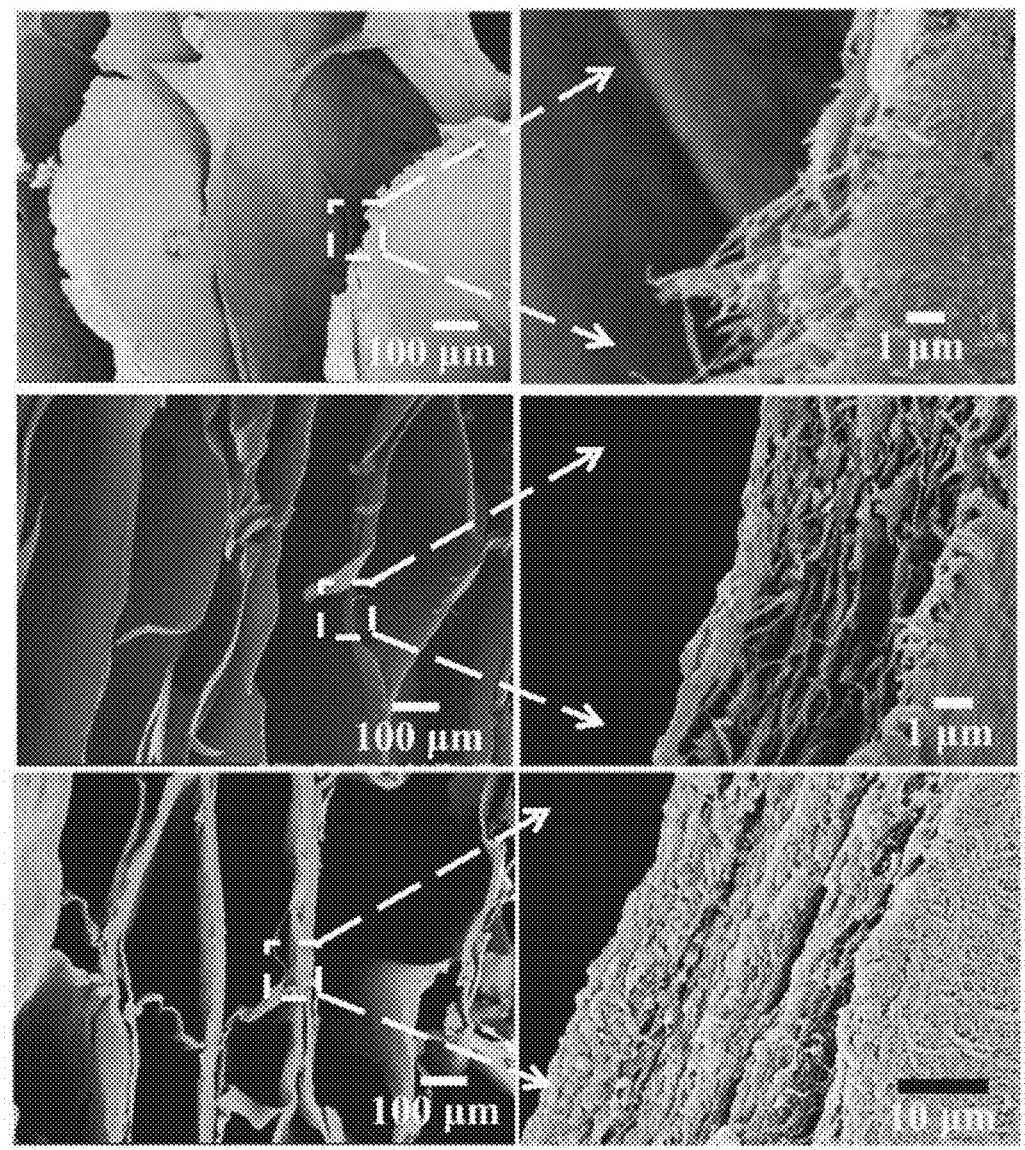
FIG. 2 shows FESEM images of cross-section parallel to the freezing direction for scaffolds fabricated by freezing the hydrogel at a constant freezing temperature of −25° C., but with a collagen density of (a) 2.5 g/L, (b) 3.9 g/L and (c) 10.5 g/L.

The scaffold exhibits a unique multi-level lamellar structure in which nano and submicron pores in each lamella and macro pores are co-aligned. This multi-level lamellar structure may lead to higher active surface area, improved permeability of oxygen and nutrients, and faster removal of metabolic waster compared to conventional uniaxial pore structure. Another unique property of the scaffold is the combination of a long-range ordered surface morphology and 3-dimensional porous structure. The surface of the scaffold is comprised of mineralized collagen fibrils with a length of over a few millimeters. The mineralized collagen fibrils further organized into big bundles and the diameter of which can be tailored by gelation conditions in terms of temperature and initial collagen concentration. FIG. 2 shows FESEM images of cross-section parallel to the freezing direction for scaffolds fabricated by freezing the hydrogel at a constant freezing temperature of −25° C., but with a collagen density of (a) 2.5 g/L, (b) 3.9 g/L and (c) 10.5 g/L.

To the best of our knowledge, this is the first report of a process to engineer three dimensional collagen-apatite hybrid scaffolds with controllable pore size and pore orientation from nano-scale to the macro-scale. With an increase of collagen density from 2.5 to 10.5 g/L, lamellar spacing decreased from 343.5±32.7 μm to 142.9±40.1 μm and wall thickness increased from 3.6±1.0 μm to 23.2±10.2 μm.

TABLE 1

Compression modulus of collagen-apatite scaffolds

| Collagen density in the hydrogel (g/L) | Compression modulus (kPa)-X | Compression modulus (kPa)-Z |
|---|---|---|
| 2.5 | 222.6 ± 69.1 | 59.5 ± 10.3 |
| 3.9 | 2912.5 ± 802.0 | 149.9 ± 25.6 |

Figure 3:
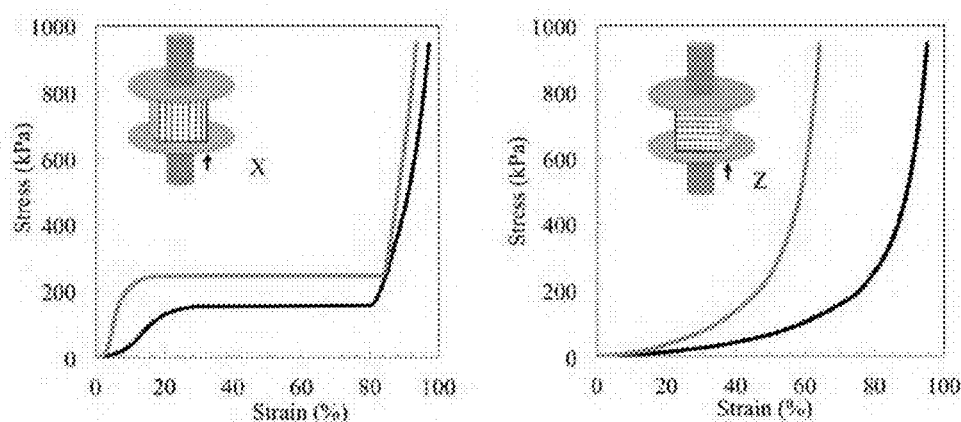
FIG. 3 shows representative unconfined compressive stress-strain curves of collagen-apatite scaffolds.

FIG. 3 shows representative unconfined compressive stress-strain curves of collagen-apatite scaffolds. The stress-strain curve of the scaffolds under compression along the pore direction was similar to cancellous bone. The increase of collagen-apatite hydrogel density leads to an increase in the compression modulus (Table 1). Therefore, the mechanical strength of the scaffold could be greatly improved by increasing the initial collagen fibril density within the hydrogel. Uniaxial tensile test performed on collagen and collagen-apatite scaffold indicated that the addition of apatite increases the Young's modulus of collagen scaffold (Table 2).

TABLE 2

Young's modulus of collagen and collagen-apatite scaffold

| Sample | Collagen density in the hydrogel (g/L) | Young's modulus (MPa) |
|---|---|---|
| Collagen | 3.9 | 13.9 ± 7.4 |
| Collagen-apatite | 3.9 | 263.8 ± 72.1 |

Figure 4:
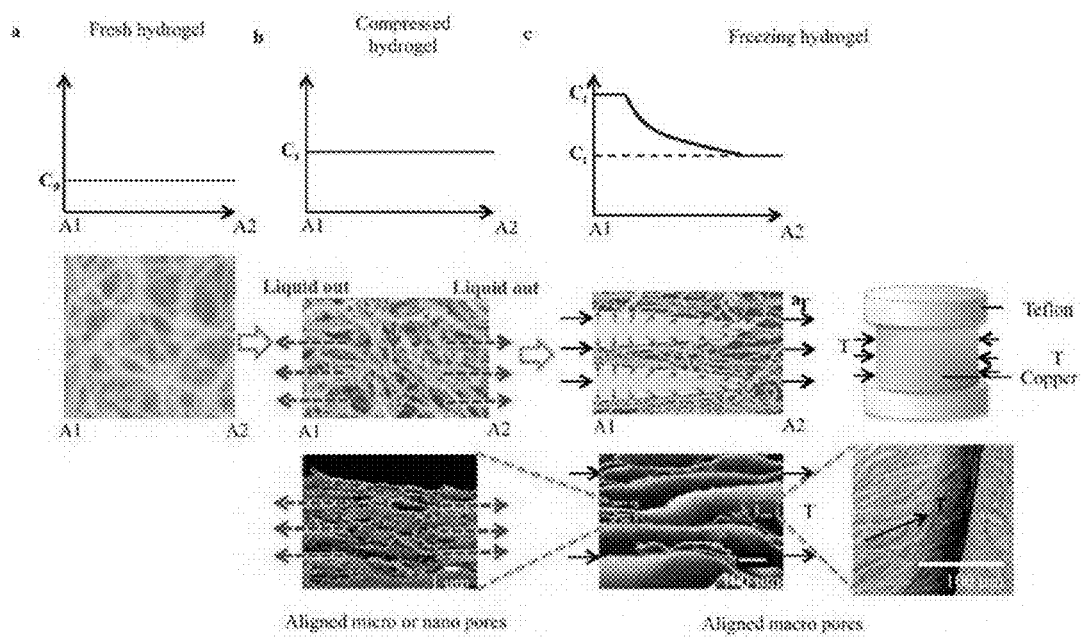
FIG. 4 shows a schematic presentation of a method to prepare a collagen-apatite scaffold: a) fresh hydrogel, b) compression of the hydrogel and c) freezing of the compressed hydrogel. $C_0$: initial collagen concentration in the hydrogel, Ct: collagen concentration in the hydrogel after self-compression for a certain period of time (t), $C_f$: collagen concentration in the frozen gel.

FIG. 4 is a schematic presentation of a method including gelation, compression and unidirectional freezing to prepare the collagen-apatite scaffolds with a multi-level lamellar structure. $C_0$: initial collagen concentration in the hydrogel, $C_t$: collagen concentration in the hydrogel after self-compression for a certain period of time (t), $C_f$: collagen concentration in the frozen gel.

A hydrogel with increased collagen concentration was produced using a simple self-compression method and the resulting $C_t$ is time dependent. The fresh hydrogel with a soft texture is mechanically unstable, because the compression force applied by self-gravity raised the chemical potential of water inside the hydrogel. As a result, water was exuded from the gel. The collagen fibrillar density of the gel can be easily controlled by the self-compression time (t). During the above unconfined self-compression process, the main fluid leaving surface acts as a filter along which compacted lamellae of mineralized collagen fibrils were aligned. Then the compressed hydrogel with a fibrillar concentration of $C_t$ was frozen in a mold that can control the temperature gradient in the transverse direction. The mineralized collagen fibrils were pushed by the advancing ice front therefore the Col-Ap density in the diminishing liquid increased to higher concentration ($C_f$). The ice front applied shear stress on the network of hydrogel thereby may further increase the degree of the alignment of mineralized collagen fibril arrays in each lamellae. The dendritic like surface topography in the solidification direction confirmed that aligned macro pores were created by uni-directionally freezing the hydrogel at different cooling rates from 1° C./min to 40° C./min using the house made mold.

Advantageously, the methods to produce the novel scaffold structures disclosed herein allow for one-step production of the hydrogel, allowing a fast hydrogel production. The cost of set-up to produce the scaffolds is low, and the processes are easy to scale-up. The controllable porosity should allow for drug uptake into the scaffolds. These novel scaffolds are expected to have particular utility in tissue engineering applications.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of producing a structural protein-calcium phosphate scaffold with an anisotropic lamellar pore structure, comprising
    providing a structural protein-calcium phosphate hydrogel comprising mineralized structural protein fibrils;
    compressing the structural protein-calcium phosphate hydrogel to increase the structural protein density in the hydrogel;
    freezing the hydrogel with a temperature gradient in a transverse direction across the hydrogel; and
    drying the frozen hydrogel to produce the structural protein-calcium phosphate scaffold with an aligned lamellar structure.

2. The method of claim 1, wherein compression is unconfined self-compression.

3. The method of claim 2, wherein self-compression is performed at a temperature of 4 to 45° C.

4. The method of claim 1, wherein the freezing temperature is −197° C. to −10° C.

5. The method of claim 4, wherein the freezing takes place over 0.5 to 4 hours.

6. The method of claim 1, wherein the structural protein is collagen Type I, II, III, or V.

7. The method of claim 6, wherein the calcium phosphate is hydroxylapatite.

8. The method of claim 1, wherein the structural protein-calcium phosphate scaffold with an anisotropic lamellar pore structure has a structural protein content of 40 to 99 wt %.

9. The method of claim 1, further comprising crosslinking the structural protein-calcium phosphate scaffold after drying.

10. The method of claim 1, wherein the structural protein-calcium phosphate hydrogel is formed by
    forming an aqueous system comprising a structural protein, a weak acid, water, $Ca^{2+}$, $HPO_4^{2-}$, a buffer system, and optionally one or more of $Mg^{2+}$, $Na^+$, $K^+$, $Cl^-$, $SO_4^{2-}$; or $HCO_3^-$;
wherein the aqueous system has an initial pH of about 6.0 to about 8.0, in a container; and
    allowing the structural protein-calcium phosphate hydrogel to form in the container at a temperature of 4-45° C. and a time of greater than one hour.

11. The method of claim 10, wherein the hydrogel is formed in a period of greater than 10 hours.

12. The method of claim 10, wherein
    the structural protein is collagen Type I present in an amount of 1 g/L to 10.0 g/L of the aqueous system;
    $Ca^{2+}$ is present in an amount of 0.1 to 30.0 mM;
    $Mg^{2+}$ is present in an amount of 0.05 to 10.0 mM;
    $Na^+$ is present in an amount of 5.0 to 300.0 mM;
    $K^+$ is present in an amount of 0.1 to 20.0 mM;
    $Cl^-$ is present in an amount of 5.0 to 300.0 mM;
    $SO_4^{2-}$ is present in an amount of 0 to 5.0 mM;
    $HPO_4^{2-}$ is present in an amount of 0.05 to 20.0 mM; and
    $HCO_3^-$ is present in an amount of 0.5 to 50.0 mM.

13. The method of claim 1, wherein the transverse temperature gradient is formed from the outer edges to the center of the hydrogel.

14. The product of the process of claim 1.

15. A biomimetic structural protein-calcium phosphate scaffold with an anisotropic lamellar pore structure produced by the process of claim 1,
    wherein at the macro-level, the scaffold comprises an anisotropic lamellar pore structure and a co-aligned macro-pore size of 10 to 350 micrometers, and
    at the micro-level each lamella of the lamellar structure comprises uniaxial aligned layers of structural protein fibers mineralized with the calcium phosphate having a pore size of less than 1 micrometer.

16. The biomimetic structural protein-calcium phosphate scaffold of claim 15, wherein the scaffold protein is collagen and the calcium phosphate is hydroxyl apatite.

17. The biomimetic structural protein-calcium phosphate scaffold of claim 16, wherein the wall thickness of the lamellar layers is 2 to 30 micrometers.

18. The biomimetic structural protein-calcium phosphate scaffold of claim 15, further comprising a drug.

19. A method of bone repair, comprising contacting the scaffold of claim 15 with osteoprogenitor cells, bone marrow cells, or both, under conditions suitable to repair bone.

20. The method of claim 19, wherein bone repair comprises new bone formation, bone-redistribution, bone-host integration, scaffold degradation, or a combination thereof.

* * * * *